US009568641B2

(12) United States Patent
Simcock et al.

(10) Patent No.: US 9,568,641 B2
(45) Date of Patent: Feb. 14, 2017

(54) IN-SITU CALIBRATION OF TOOLS (71) Applicant: Halliburton Energy Services, Inc., Houston, TX (US)

(72) Inventors: Michael Neil Simcock, Columbia, SC (US); David L. Perkins, The Woodlands, TX (US)

(73) Assignee: Halliburton Energy Services, Inc., Houston, TX (US)

( * ) Notice: Subject to any disclaimer, the term of this patent is extended or adjusted under 35 U.S.C. 154(b) by 0 days.

(21) Appl. No.: 14/769,817

(22) PCT Filed: Mar. 28, 2013

(86) PCT No.: PCT/US2013/034273
§ 371 (c)(1),
(2) Date: Aug. 23, 2015

(87) PCT Pub. No.: WO2014/158160
PCT Pub. Date: Oct. 2, 2014

(65) Prior Publication Data
US 2016/0003970 A1  Jan. 7, 2016

(51) Int. Cl.
*G01V 8/12* (2006.01)
*E21B 49/08* (2006.01)
(Continued)

(52) U.S. Cl.
CPC .............. *G01V 8/12* (2013.01); *E21B 47/00* (2013.01); *E21B 47/102* (2013.01);
(Continued)

(58) Field of Classification Search
CPC .......... G01V 8/12; E21B 49/087; E21B 47/00; E21B 47/102; G01N 21/85; G01N 21/276
(Continued)

(56) References Cited

U.S. PATENT DOCUMENTS 3,950,104 A * 4/1976 Munk .................... G01N 21/41
356/128
4,167,665 A  9/1979 Johns et al.
(Continued)

FOREIGN PATENT DOCUMENTS

WO  96/06345 A1  2/1996
WO  2004/104554 A2  12/2004
(Continued)

OTHER PUBLICATIONS

International Search Report and Written Opinion issued in related PCT Application No. PCT/US2013/034273 mailed Jan. 3, 2014, 11 pages.
(Continued)

*Primary Examiner* — Sang Nguyen
(74) *Attorney, Agent, or Firm* — Benjamin Fite; Baker Botts L.L.P.

(57) ABSTRACT

A tool sensor calibration system and tool calibration method are disclosed herein. A tool sensor calibration system (200) comprises a flow pipe (206), an isolation cell (214) in fluid communication with the flow pipe, a sensor (210) positioned proximate to the isolation cell, a fluid chamber (213) containing a reference fluid (212) with a known property value, and a first valve (222a) coupled to the fluid chamber that provides selective fluid communication between the fluid chamber and the flow pipe. A tool calibration method comprises introducing a first fluid (208) into a flow pipe, introducing a reference fluid into the flow pipe from a fluid chamber in fluid communication with the flow pipe through a valve, wherein the first fluid and the reference fluid mix to form a composite fluid, and detecting a property of the composite fluid at an isolation cell in fluid communication with the flow pipe.

19 Claims, 4 Drawing Sheets

(51) Int. Cl.
*E21B 47/00* (2012.01)
*E21B 47/10* (2012.01)
*G01N 21/27* (2006.01)
*G01N 21/85* (2006.01)

(52) U.S. Cl.
CPC ......... *E21B 49/087* (2013.01); *G01N 21/276* (2013.01); *G01N 21/85* (2013.01)

(58) Field of Classification Search
USPC .................................. 356/432–444; 73/1.03
See application file for complete search history.

(56) References Cited

U.S. PATENT DOCUMENTS

| | | | | |
|---|---|---|---|---|
| 4,462,962 | A * | 7/1984 | Baba | G01N 30/64 |
| | | | | 210/198.2 |
| 5,068,542 | A * | 11/1991 | Ando | G01N 21/85 |
| | | | | 250/573 |
| 5,835,230 | A | 11/1998 | McAndrew et al. | |
| 5,859,430 | A | 1/1999 | Mullins et al. | |
| 5,995,209 | A * | 11/1999 | Ohman | G01N 21/05 |
| | | | | 356/246 |
| 6,188,813 | B1 * | 2/2001 | Dourdeville | G01N 21/05 |
| | | | | 250/227.11 |
| 2010/0263862 | A1 * | 10/2010 | Goodwin | E21B 47/06 |
| | | | | 166/252.5 |
| 2011/0061439 | A1 | 3/2011 | Dong et al. | |
| 2011/0071810 | A1 * | 3/2011 | Yeriazarian | G05D 7/06 |
| | | | | 703/10 |
| 2012/0127470 | A1 | 5/2012 | Chumachenko et al. | |
| 2012/0250014 | A1 | 10/2012 | Hayashi et al. | |
| 2013/0033702 | A1 * | 2/2013 | Tunheim | G01N 21/85 |
| | | | | 356/73 |

FOREIGN PATENT DOCUMENTS

| | | |
|---|---|---|
| WO | 2006/063094 A1 | 6/2006 |
| WO | 2013/033198 A1 | 3/2013 |

OTHER PUBLICATIONS

International Preliminary Report on Patentability issued in related PCT Application No. PCT/US2013/034273 mailed Jun. 16, 2015, 17 pages.
Second Written Opinion issued in related PCT Application No. PCT/US2013/034273 mailed Feb. 25, 2015, 11 pages.

* cited by examiner

IN-SITU CALIBRATION OF TOOLS

CROSS-REFERENCE TO RELATED APPLICATION

The present application is a U.S. National Stage Application of International Application No. PCT/US2013/034273 filed Mar. 28, 2013, which is incorporated herein by reference in its entirety for all purposes.

BACKGROUND

This disclosure relates generally to tools located in a wellbore, and more particularly concerns a system and method of calibrating tools used to detect fluids and gases, and components thereof, in a downhole environment.

It is often desirable to monitor the properties of hydrocarbons retrieved from a subterranean formation in-situ. For instance, with respect to petroleum, it may be desirable to monitor a number of physical qualities, such as, for example: phase (oil, water, gas, solids), density, viscosity, bubble point, petroleum formation factor, and reservoir continuity. Other important fluid chemical properties that may be monitored in reservoir fluids include, for example: concentrations of methane, ethane, propane, butane, pentane, oxygen, $CO_2$, $H_2S$; GOR (gas oil ratio); saturate, aromatic, resin and asphaltene (SARA) composition; water content and chemistry (ions and pH); and other contaminants (e.g., mud filtrate).

However, the tools used to monitor hydrocarbons in a well are often not calibrated adequately to be able to make accurate measurements. This may be, for example, because the fluid or gas in the sample may not be at a concentration high enough to be measured, the fluid or gas in the measured sample may be below the limit of detection by the tool, or there may be contamination (e.g., from drilling fluid in the wellbore) in the sample that interferes with the instruments' detection method. Additionally, tools that are calibrated may need to be recalibrated once positioned downhole, to account for instrumental drift due to changes in temperature and pressure at which the tool must operate in the wellbore. Accordingly, it is desirable to be able to calibrate a tool in-situ to take measurements of a sample without needing to raise it to the surface.

BRIEF DESCRIPTION OF THE DRAWINGS

The present disclosure will be more fully understood by reference to the following detailed description of the preferred embodiments of the present disclosure when read in conjunction with the accompanying drawings, in which like reference numbers refer to like parts throughout the views, wherein.

The disclosure may be embodied in other specific forms without departing from the spirit or essential characteristics thereof. The present embodiments are therefore to be considered in all respects as illustrative and not restrictive, the scope of the disclosure being indicated by the appended claims rather than by the foregoing description, and all changes which come within the meaning and range of equivalency of the claims are therefore intended to be embraced therein.

DETAILED DESCRIPTION OF THE DISCLOSURE

Illustrative embodiments of the present invention are described in detail herein. In the interest of clarity, not all features of an actual implementation may be described in this specification. It will of course be appreciated that in the development of any such actual embodiment, numerous implementation-specific decisions may be made to achieve the specific implementation goals, which may vary from one implementation to another. Moreover, it will be appreciated that such a development effort might be complex and time-consuming, but would nevertheless be a routine undertaking for those of ordinary skill in the art having the benefit of the present disclosure.

The terms "couple" or "couples," as used herein are intended to mean either an indirect or a direct connection. Thus, if a first device couples to a second device, that connection may be through a direct connection, or through an indirect electrical or mechanical connection via other devices and connections. The term "upstream" as used herein means along a flow path towards the source of the flow, and the term "downstream" as used herein means along a flow path away from the source of the flow. The term "uphole" as used herein means along the drillstring or the wellbore from the distal end towards the surface, and "downhole" as used herein means along the drillstring or the wellbore from the surface towards the distal end.

For the purposes of this disclosure, computer-readable media may include any instrumentality or aggregation of instrumentalities that may retain data and/or instructions for a period of time. Computer-readable media may include, for example, without limitation, storage media such as a direct access storage device (e.g., a hard disk drive or floppy disk drive), a sequential access storage device (e.g., a tape disk drive), compact disk, CD-ROM, DVD, RAM, ROM, electrically erasable programmable read-only memory (EEPROM), and/or flash memory; and/or any combination of the foregoing.

For purposes of this disclosure, an information handling system may include any instrumentality or aggregate of instrumentalities operable to compute, classify, process, transmit, receive, retrieve, originate, switch, store, display, manifest, detect, record, reproduce, handle, or utilize any form of information, intelligence, or data for business, scientific, control, or other purposes. For example, an information handling system may be a personal computer, a network storage device, or any other suitable device and may vary in size, shape, performance, functionality, and price. The information handling system may include random access memory (RAM), one or more processing resources such as a central processing unit (CPU), hardware or software control logic, ROM, and/or other types of nonvolatile memory. Additional components of the information handling system may include one or more disk drives, one or more network ports for communication with external devices as well as various input and output (I/O) devices, such as a keyboard, a mouse, and a video display. The information handling system may also include one or more buses operable to transmit communications between the various hardware components.

It will be understood that the term "oil well drilling equipment" or "oil well drilling system" is not intended to limit the use of the equipment and processes described with those teems to drilling an oil well. The terms also encompass drilling natural gas wells or hydrocarbon wells in general. Further, such ;wells can be used for production, monitoring, or injection in relation to the recovery of hydrocarbons or other materials from the subsurface. This could also include geothermal wells intended to provide a source of heat energy instead of hydrocarbons. Embodiments of the present disclosure may be applicable to horizontal, vertical, deviated, or otherwise nonlinear wellbores in any type of subterranean formation.

To facilitate a better understanding of the present disclosure, the following examples of certain embodiments are given. In no way should the following examples be read to limit, or define, the scope of the disclosure. Embodiments of the present disclosure may be applicable to horizontal, vertical, deviated, multilateral, u-tube connection, intersection, bypass (drill around a mid-depth stuck fish and back into the wellbore below), or otherwise nonlinear wellbores in any type of subterranean formation. Certain embodiments may be applicable, for example, to logging data acquired with tools deployed via wireline, slickline, or coiled tubing, and/or logging date acquired via logging while drilling/measurement while drilling (LWD/MWD). Certain embodiments may be applicable to subsea and/or deep sea wellbores. Embodiments described below with respect to one implementation are not intended to be limiting.

Figure 1A:
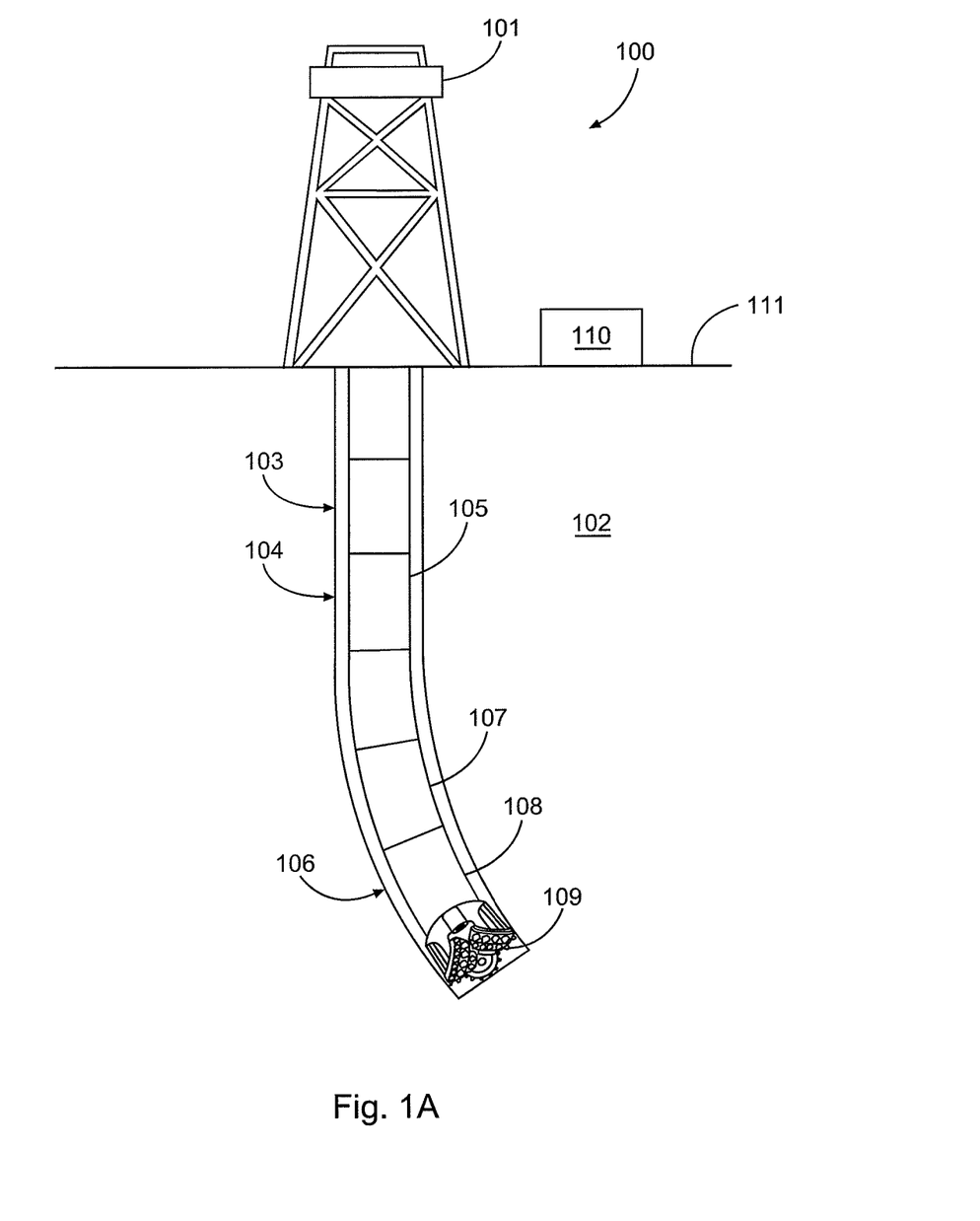
FIG. 1A depicts an example drilling system, according to aspects of the present disclosure.

FIG. 1 A illustrates an example drilling system 100, according to aspects of the present disclosure. The drilling system 100 includes a rig 101 located at a surface 111 and positioned above a wellbore 103 within a subterranean formation 102. In certain embodiments, a drilling assembly 104 may be coupled to the rig 101 via a drill string 105. The drilling assembly 104 may include a bottom hole assembly (BHA) 106. The BHA 106 may include a drill bit 109, a steering assembly 108, and a LWD/MWD apparatus 107. A control unit 110 located at the surface 111 may include a processor and memory device, and may communicate with elements of the BHA 106, in the LWD/MWD apparatus 107 and the steering assembly 108. The control unit 110 may receive data from and send control signals to the BHA 106. Additionally, at least one processor and memory device may be located downhole within the BHA 106 for the same purposes. The LWD/MWD apparatus 107 may log the formation 102 both while the wellbore 103 is being drilled, and after the wellbore is drilled to optimize fracture locations. The steering assembly 108 may include a rotary steerable drilling system that controls the direction in which the wellbore 103 is being drilled, and that is rotated along with the drill string 105 during drilling operations. In certain embodiments, the steering assembly 108 may angle the drill bit 109 to drill at an angle from the wellbore 103. Maintaining the axial position of the drill bit 109 relative to the wellbore 103 may require knowledge of the rotational position of the drill bit 109 relative to the wellbore 103.

Figure 1B:
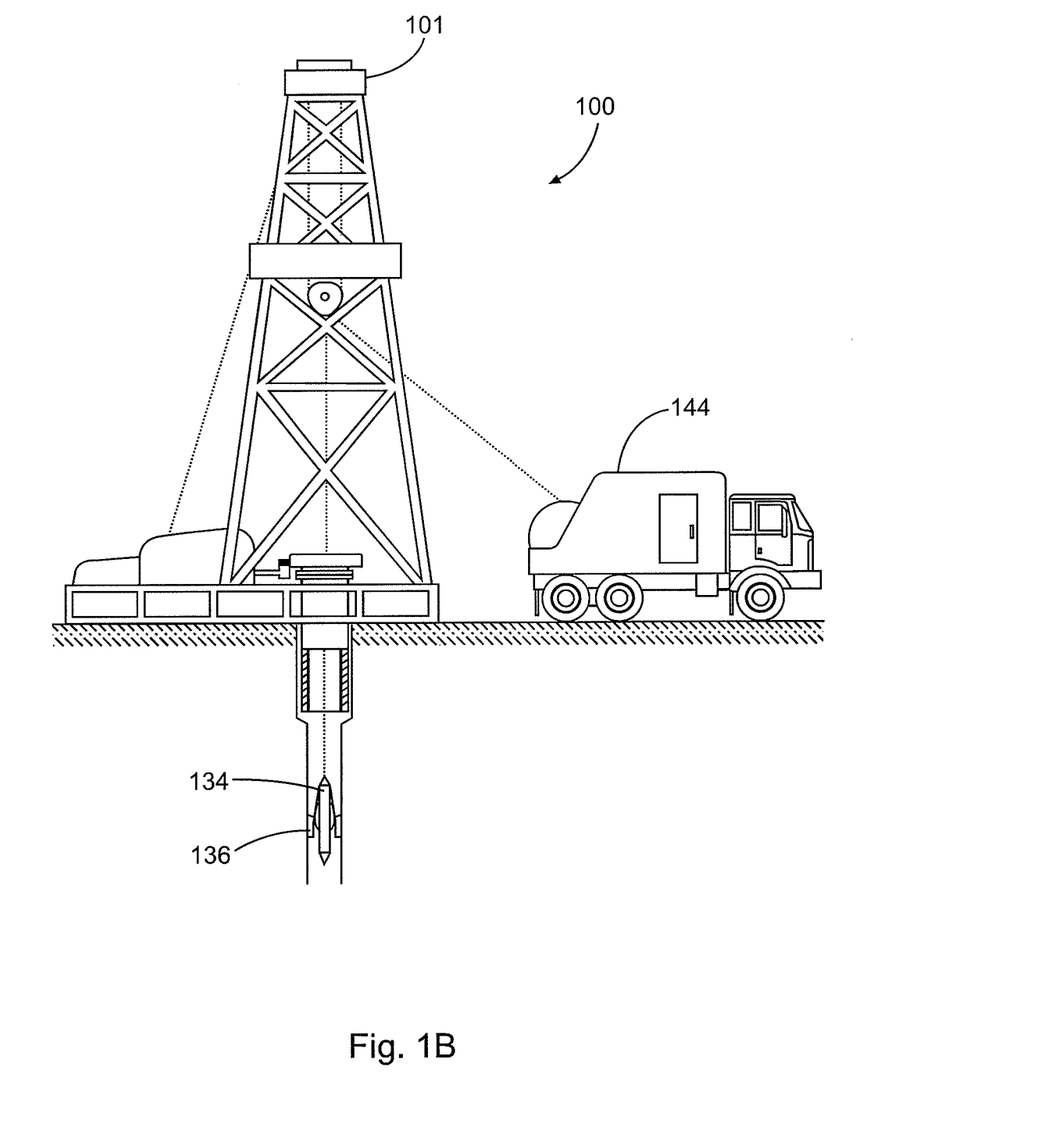
FIG. 1B depicts an example wireline system, according to aspects of the present disclosure.

Referring now to FIG. 1B, at various times, logging operations can be conducted using a wireline logging tool 134, i.e., a sensing instrument sonde suspended by a cable having conductors for transporting power to the tool and telemetry from the tool to the surface. A resistivity imaging portion of the logging tool 134 may have centralizing arms 136 that center the tool within the borehole as the tool is pulled uphole. A logging facility 144 may collect measurements from the logging tool 134, and may include computing facilities for processing and storing the measurements gathered by the logging tool.

Figure 2:
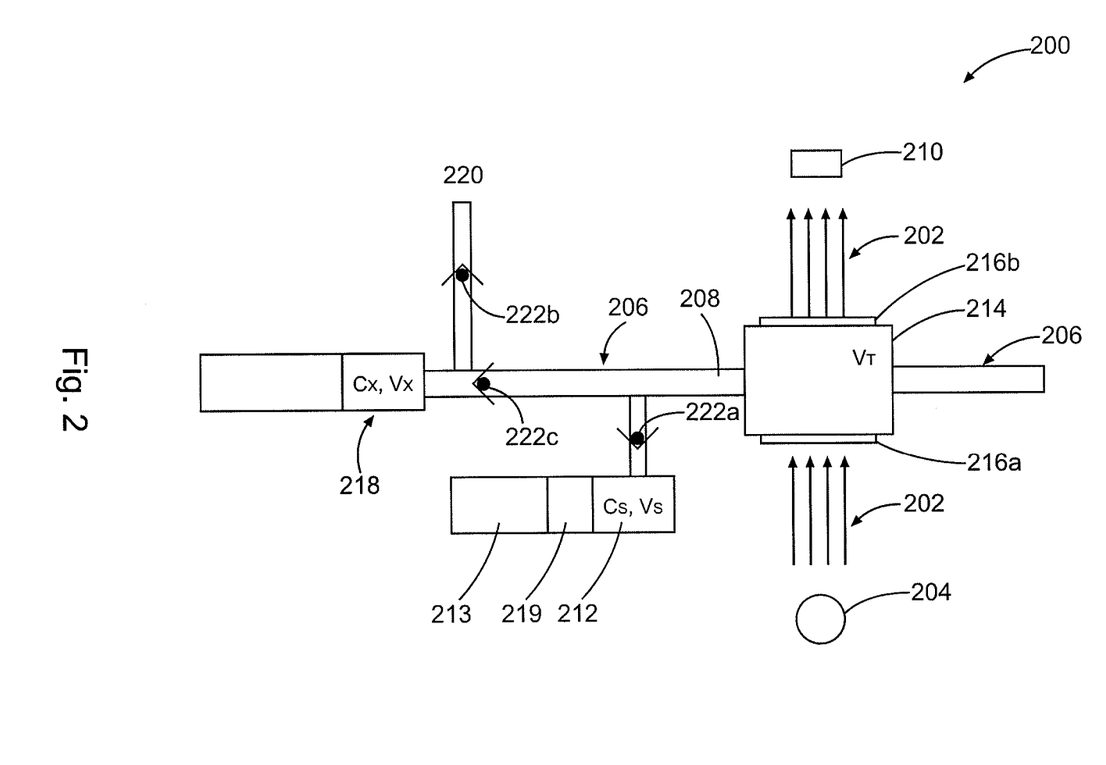
FIG. 2 depicts a system for performing optical analysis in accordance with an illustrative embodiment of the present disclosure.

Referring now to FIG. 2, an exemplary system for performing fluid analysis is referenced generally by reference numeral 200. In particular, the system 200 performs optical fluid analysis, but other fluid analysis systems might be used without departing from the scope of this disclosure. The system 200 may be incorporated into the drilling assembly 104 and lowered downhole via drill string 105. Alternatively, the system 200 may be lowered downhole by wireline, slickline, or coiled tubing, or by any other means known to those in the art having the benefit of this disclosure. Alternatively, the system 200 may be positioned downhole for permanent monitoring during wellbore drilling and completion operations.

Still referring to FIG. 2, a light source 204 is located on one side of a flow pipe 206 containing a first fluid 208. The light source 204 may include any associated optics. In the embodiment shown, the system 200 may be used to identify certain properties of the first fluid 208. Thus, the isolation cell 214 may be in fluid communication with the flow pipe 206. The flow pipe 206 may be a casing, pipe or tubing used to convey fluid 208 to an isolation cell 214. The flow pipe 206 may be at least partially disposed within the isolation cell 214. The isolation cell 214 may be used for fluid and/or gas mixing and is configured to contain fluids or gases for measurements and light transmission. A sensor 210 and the light source 204 may each be positioned proximate to the isolation cell 214. The sensor 210 may be located on the opposite side of the flow pipe 206 from the light source 204 as shown in FIG. 2. However, the sensor 210 may also be located on the same side of the flow pipe 206 as the light source 204 without departing from the scope of this disclosure. In the embodiment shown in FIG. 2, the sensor 210 is an optical sensor. The sensor 210 may also be an optical transducer. The isolation cell 214 includes two transparent windows 216a and 216b to isolate the first fluid 208 from the light source 204 and the sensor 210. A fluid chamber 213 may be coupled to the isolation cell 214 via the flow pipe 206. The fluid chamber 213 contains a reference fluid 212 of known property value. The known property value of the reference fluid 212 may include at least one of: chemical concentration, phase, density, temperature, resistance, capacitance, viscosity, bubble point, petroleum formation factor, or reservoir continuity. A first valve 222a may be coupled to the fluid chamber 213. The first valve 222a may provide selective fluid communication between the fluid chamber 213 and the flow pipe 206. The fluid chamber 213 may be coupled to a first reciprocating pump 219. A hydrocarbon reservoir 220 may be coupled to the flow pipe 206 via a second valve 222b. The hydrocarbon reservoir 220 is a geological formation reservoir in an underground or subsea formation. The hydrocarbon reservoir 220 may contain the first fluid 208. The flow pipe 206 may be coupled to a second reciprocating pump 218 that introduces the first fluid 208 into the flow pipe 206 from the hydrocarbon reservoir 220 at a known volume. The second reciprocating pump 218 may be coupled to the flow pipe 206 via a third valve 222c. While the system in FIG. 2 performs optical analysis, tools of other applications may be used without departing from the scope of this disclosure. For example, a tool may include any device lowered into a wellbore used to take a reading of a fluid.

In operation of the system 200, electromagnetic radiation 202 may be directed from the light source 204 through the first window 216a to the isolation cell 214 containing a composite fluid. The composite fluid may include the first fluid 208 and the reference fluid 212. At least a portion of the electromagnetic radiation 202 may travel through the second window 216b and then to the sensor 210. In some embodiments, the electromagnetic radiation 202 may travel to an optical element (not shown), which may direct the electromagnetic radiation 202 to the sensor 210. Thus, the sensor 210 and the optical element are in optical communication. The optical element may include, but is not limited to, an Integrated Computational Element (ICE). The ICE may be operable to distinguish electromagnetic radiation 202 relating to the concentration of the first fluid 208 from electromagnetic radiation 202 related to other components of the composite fluid (i.e., the reference fluid 212). The sensor 210 detects the electromagnetic radiation 202 as input and may make readings about the first fluid 208 based on the electromagnetic radiation 202. The output of the sensor 210 is a signal (e.g., a voltage, a current, a pressure pulse, or other waveform) that may be correlated to a property of interest of the first fluid 208. A property of interest may include, but is not limited to, phase, density, viscosity, bubble point, petroleum formation factor, and reservoir continuity. This output may be converted to an appropriate signal for communication purposes via standard electronics. The operation of such electronic systems is well known to those of ordinary skill in the art, having the benefit of the present disclosure, and will therefore not be discussed in detail herein. The property or concentration result, in real time, may be displayed. It may also be employed in an active feedback loop to control the property or concentration of interest of the first fluid 208 or may be used to alert for certain desired conditions, such as out of range condition, or interrupted flow. For example, the concentration of the first fluid 208 may be adjusted to the desired conditions based on the output from the sensor 210. In some embodiments, a second sensor (not shown) may be used to normalize the signal of the sensor 210 for light intensity variations, scattering effects, and the like.

However, in some cases the concentration of the fluid 208 in the flow pipe 206 is too small to be detected by the sensor 210. Additionally, in some cases the temperature of the system may cause the sensor signal to drift, resulting in inaccurate performance. Therefore, the sensor 210 may not be properly calibrated to detect the property or concentration of interest of the fluid 208. In these cases, the reference fluid 212 may be introduced at a known volume and known property value to the flow pipe 206. The known property value of the reference fluid 212 may include at least one of: chemical concentration, phase, density, temperature, resistance, capacitance, viscosity, bubble point, petroleum formation factor, or reservoir continuity. The reference fluid 212 may be contained within the fluid chamber 213 and then controllably released into the flow pipe 206. The volume of the reference fluid 212 released from the fluid chamber 213 may be measured by the valve 222a or any other known means. Alternatively, the reference fluid 212 may be released from the fluid chamber 213 using the first reciprocating pump 219 with a fixed and/or variable stroke. The volume of the reference fluid 212 in this case is controlled by a combination of the number of stoke cycles and stroke length of the first reciprocating pump 219. The reference fluid 212 may include, but is not limited to, a fluid, such as hexane, or a gas, such as methane. The reference fluid 212 may mix with the first fluid 208 in the isolation cell 214 to form a composite fluid. The first fluid 208 may be continuously pumped using a second reciprocating pump 218 at known volumes through the flow pipe 206 and isolation cell 214 from a hydrocarbon reservoir 220. The direction of fluid flow in the flow pipe 206 is controlled by valves 222a,b,c. As the electromagnetic radiation 202 passes through the composite fluid in the isolation cell 214, the sensor 210 may record information. The sensor 210 may detect the electromagnetic radiation 202 as input and may make readings about the first fluid 208 based on the electromagnetic radiation 202. The output of the sensor 210 may be correlated to the property or concentration of interest of the first fluid 208. This output may be converted to an appropriate signal for communication purposes via standard electronics. It may also be employed in an active feedback loop to control the property or concentration of interest of the first fluid 208 or may be used to alert for certain desired conditions, such as out of range condition, or interrupted flow. In some embodiments, a second sensor (not shown) may be used to normalize the signal of the sensor 210 for light intensity variations, scattering effects, and the like. Using the standard addition method known to those of skill in the art having the benefit of this disclosure as detailed below in Equations 1-8, a series of measurements and mathematical calculations may be performed in order to calibrate the sensor 210 for future measurements of the first fluid 208. Other optical arrangements known to those skilled in the art may be implemented without departing from the scope of this disclosure, for example, optical transmissions, reflection, diffuse reflection, and scattering.

EXAMPLE

In this example, a user may want to know the chemical concentration $C_x$ of a first fluid 208, where the chemical concentration $C_s$ of a reference fluid 212 is known. However, the same system, method, and set of equations may be used to determine any unknown physical or chemical property value of the first fluid 208 where the same physical or chemical property value of the reference fluid 212 is known. For example, the following equations may be used to determine an unknown phase, density, temperature, resistance, capacitance, viscosity, bubble point, petroleum formation factor, or reservoir continuity of the first fluid 208 where the same property value is known of the reference fluid 212. In those instances, $C_s$ would be replaced with the known property value of the reference fluid 212 and $C_x$ would be replaced with the unknown property value of the first fluid 208.

Figure 4:
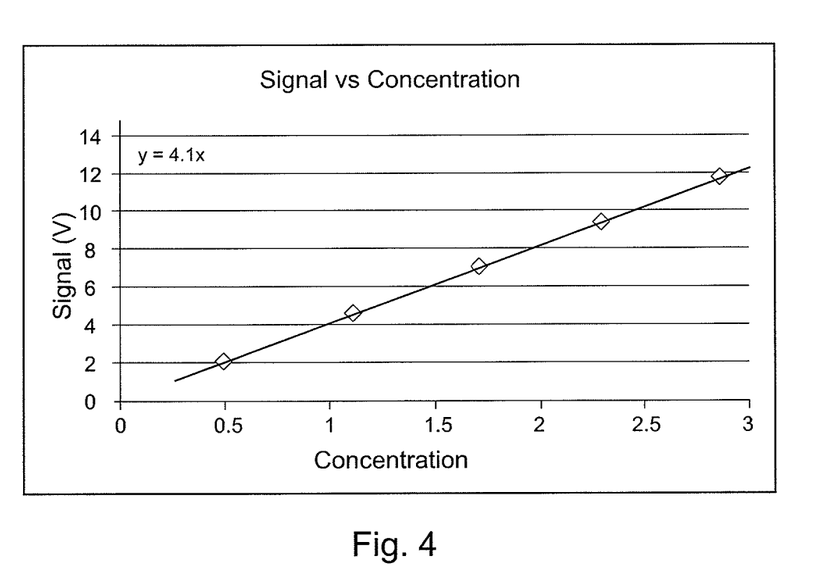
FIG. 4 depicts a plot of the signal response versus the concentration of added reference fluid in accordance with an example of an embodiment of the present disclosure.

In this example, a sample interrogation volume ($V_t$) of a downhole tool remains constant as the first fluid 208 of an unknown concentration ($C_x$) is pumped through the downhole tool 200. The sample interrogation volume $V_t$ represents either a measured or calculated volume of the region to be sampled. The region to be sampled includes the region where the electromagnetic radiation 202 interacts with the first fluid 208. It may also include the volume between valves 222a,b,c. As a known volume ($V_s$) of a reference fluid 212 with a known concentration ($C_s$) is released into the flow pipe 206 and mixes with the first fluid 208, the optical signal (S) detected at the sensor 110 may be described by Equation (1):

$$S=(kV_sC_s)/V_t+(kV_xC_x)/V_t \quad (1)$$

where k is a proportionality constant. The reference fluid 212 may be added to the flow pipe 206 at several sequential points in time. Each addition of the reference fluid 212 is made at a known volume. FIG. 4 shows a plot of the signal (S) versus the volume of several sequential reference fluid additions ($V_s$). Then, the slope (m) and intercept (b) may be calculated using Equations (2) and (3):

$$m = (kC_s)/V_t \quad (2)$$

$$b = (kV_xC_x)/V_t \quad (3)$$

The intercept (b) is the signal (S) that would be recorded at the sensor 210 if no reference fluid 212 were added to the flow pipe 206. Both m and b may be determined using a least squares fit to the data recorded by the sensor 210. $C_x$ may be calculated using Equations (4) and (5), using a ratio of b and m and known quantities $C_s$, $V_x$, and $V_s$:

$$(b/m) = ((kV_xC_x)/V_t)/(kC_s)/V_t) = (V_xC_x)/C_s \quad (4)$$

$$C_x = (bC_s)/(mV_x) \quad (5)$$

Alternatively, the plot of S versus $V_s$ can be extrapolated to the x-axis intercept $V_s(0)$. The x-intercept represents the volume of reference fluid 212 when the signal (S) at the sensor 210 is equal to 0. Therefore, Equation 1 may be set equal to zero in order to solve for $C_x$:

$$C_x = (-(V_s)0))*C_s)/V_x \quad (6)$$

Figure 3:
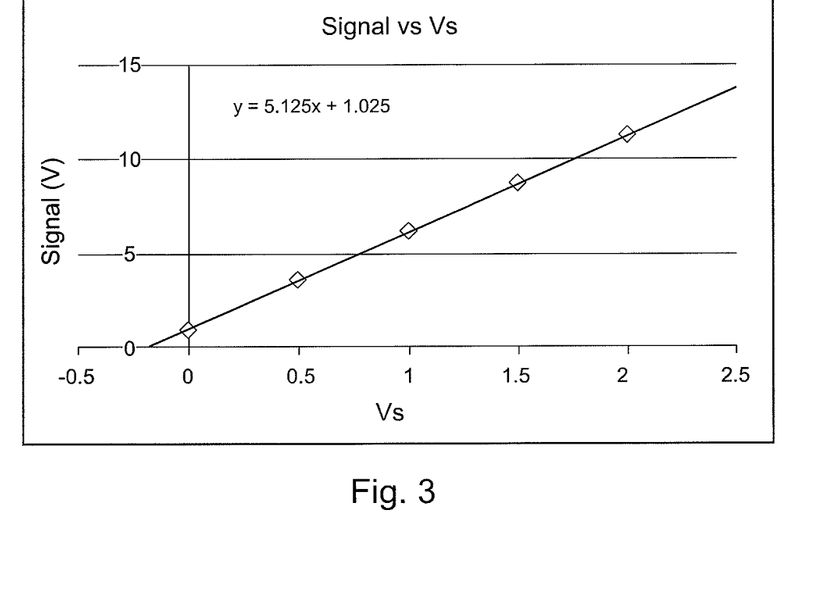
FIG. 3 depicts a plot of the signal response versus the volume of added reference fluid in accordance with an example of an embodiment of the present disclosure.

Now that the original concentration of the first fluid 208 is known ($C_x$), a new plot of S versus composite fluid concentration ($C_m$) may be generated using Equation 7 at each addition of $C_s$. This is shown in FIG. 3.

$$C_m = (V_sC_s + V_xC_x)/V_t \quad (7)$$

The slope of S versus $C_m$ is k from Equation 1, and the intercept is zero. The system 200 has been calibrated in-situ and future concentrations of the first fluid may be calculated by Equation 8:

$$C_x = S/k \quad (8)$$

This approach may account for matrix effects present in the system 200. As used in this disclosure, "matrix" refers to the components of a sample other than the first fluid 108. The matrix may have a considerable effect on the way an analysis is conducted and the quality of the results obtained; further, these effects are difficult to simulate in a traditional laboratory calibration or on the surface. For example, surface calibrations of tools may use reservoir fluid previously brought to the surface. These reservoir fluids can undergo a change in temperature and pressure in the sample containers as they are collected, transported to the surface and used as a calibration fluid in a tool. The change in temperature and pressure may cause reservoir fluid properties to change from their initial in-situ conditions. For example, temperature changes may cause precipitation of solids out of solution. Pressure changes may cause a gas or gases to come out of solution. These types of changes can result in inaccurate calibrations due to inaccurate knowledge of the calibrating fluid concentrations.

In some cases, in order to calibrate a downhole tool for some components of the first fluid 208 like methane, ethane and propane (i.e., components that often exist in solution in first fluids 208 that exist downhole) calibrations include the use of other reservoir fluids (that have had these low boiling gases previously removed for safe storage and handling) in order to incorporate matrix effects. However, adding these gases into solution in the laboratory is challenging and requires special equipment. In addition, many surface experiments are required to model the downhole matrix effects or conditions.

This disclosure may be used in applications other than an optical tool. In the case of a non-optical tool, a light source and electromagnetic radiation would not be used. A sensor may be located on or in the flow pipe 206. The sensor may be operable to detect a physical or chemical property of the composite fluid. The sensor may include, but is not limited to, a temperature sensor, a densitometer, or a viscometer.

Therefore, the present invention is well adapted to attain the ends and advantages mentioned as well as those that are inherent therein. The particular embodiments disclosed above are illustrative only, as the present invention may be modified and practiced in different but equivalent manners apparent to those skilled in the art having the benefit of the teachings herein. Furthermore, no limitations are intended to the details of construction or design herein shown, other than as described in the claims below. It is therefore evident that the particular illustrative embodiments disclosed above may be altered or modified and all such variations are considered within the scope and spirit of the present invention. Also, the terms in the claims have their plain, ordinary meaning unless otherwise explicitly and clearly defined by the patentee.

What is claimed is:

1. A tool sensor calibration system, comprising:
   a flow pipe;
   an isolation cell in fluid communication with the flow pipe, wherein the isolation cell comprises a first window and a second window, and wherein the isolation cell contains a composite fluid, wherein the composite fluid comprises a mixture of a first fluid comprising a fluid from a hydrocarbon reservoir and a reference fluid having a known property value;
   a sensor positioned proximate to the isolation cell;
   a fluid chamber coupled to the isolation cell via the flow pipe, wherein the fluid chamber contains the reference fluid; and
   a first valve coupled to the fluid chamber to provide selective fluid communication between the fluid chamber and the flow pipe.

2. The system of claim 1, wherein the sensor comprises an optical sensor.

3. The system of claim 2, further comprising an integrated computational element (ICE) in optical communication with the optical sensor.

4. The system of claim 1, wherein the flow pipe is coupled to a reservoir through a second valve, wherein the reservoir contains the first fluid.

5. The system of claim 4, further comprising a reciprocating pump coupled to the flow pipe.

6. The system of claim 5, wherein the sensor is operable to measure at least one physical or chemical property of the composite fluid.

7. The system of claim 1, wherein the known property value includes at least one of the following: chemical concentration, phase, density, temperature, resistance, capacitance, viscosity, bubble point, petroleum formation factor, and reservoir continuity.

8. A tool calibration method, comprising:
   introducing a first fluid comprising a fluid from a hydrocarbon reservoir into a flow pipe;
   introducing a reference fluid into the flow pipe;
   mixing the first fluid and the reference fluid to form a composite fluid at an isolation cell in fluid communication with the flow pipe; and
   detecting a property of the composite fluid at the isolation cell.

9. The method of claim 8, wherein the first fluid is introduced into the flow pipe at a known volume.

10. The method of claim 8, wherein the reference fluid is introduced to the flow pipe at a known volume and known property value.

11. The method of claim 10, wherein the known property value includes at least one of the following: chemical concentration, phase, density, temperature, resistance, capacitance, viscosity, bubble point, petroleum formation factor, and reservoir continuity.

12. The method of claim 10, wherein detecting a property of the composite fluid at the isolation cell comprises:
outputting a signal relating to a property of the composite fluid from a sensor to a processor;
performing at least one mathematical operation on the output signal.

13. The method of claim 12, wherein performing at least one mathematical operation comprises performing standard addition.

14. The method of claim 10, further comprising:
passing electromagnetic radiation through the composite fluid at the isolation cell; and
detecting the electromagnetic radiation passed through the composite fluid at the sensor.

15. The method of claim 14, further comprising:
directing the detected electromagnetic radiation from the isolation cell to an integrated computational element (ICE).

16. The method of claim 14, further comprising:
distinguishing electromagnetic radiation relating to the concentration of the first fluid from electromagnetic radiation related to other components of the composite fluid.

17. The method of claim 14, further comprising:
providing an output at the sensor, wherein the output is correlated to a property of interest of the first fluid.

18. The method of claim 17, further comprising:
employing the sensor output in a feedback loop;
controlling the property or concentration of interest of the first fluid based on the sensor output.

19. The method of claim 8, wherein the property of the composite fluid includes at least one of the following: chemical concentration, phase, density, temperature, resistance, capacitance, viscosity, bubble point, petroleum formation factor, and reservoir continuity.

* * * * *